(12) United States Patent
    Suda

(10) Patent No.: US 9,039,709 B2
(45) Date of Patent: May 26, 2015

(54) PUNCTURE INSTRUMENT

(71) Applicant: Kota Suda, Sapporo (JP)

(72) Inventor: Kota Suda, Sapporo (JP)

(73) Assignee: Kota Suda, Hokkaido (JP)

( * ) Notice: Subject to any disclaimer, the term of this patent is extended or adjusted under 35 U.S.C. 154(b) by 0 days.

(21) Appl. No.: 14/174,337

(22) Filed: Feb. 6, 2014

(65) Prior Publication Data

US 2014/0155898 A1    Jun. 5, 2014

Related U.S. Application Data

(63) Continuation of application No. PCT/JP2012/051091, filed on Jan. 19, 2012.

(30) Foreign Application Priority Data

Aug. 10, 2011    (JP) .................................. 2011-175072

(51) Int. Cl.
    *A61B 17/32*        (2006.01)
    *A61B 17/00*        (2006.01)
    *A61B 17/16*        (2006.01)
    *A61B 17/3205*      (2006.01)
    *A61B 19/00*        (2006.01)

(52) U.S. Cl.
    CPC ....... *A61B 17/1604* (2013.01); *A61B 17/32053* (2013.01); *A61B 2017/320056* (2013.01); *A61B 17/1671* (2013.01); *A61B 2019/306* (2013.01)

(58) Field of Classification Search
    CPC ............. A61B 2017/320056; A61B 17/32053; A61B 17/1604; A61B 17/1671
    USPC .............................. 606/185, 184, 172; 433/72
    See application file for complete search history.

(56) References Cited

U.S. PATENT DOCUMENTS 4,239,045 A * 12/1980 Schlein ........................... 606/83
4,621,630 A    11/1986 Kenna
(Continued)

FOREIGN PATENT DOCUMENTS

CN    101869506    10/2010
JP    2009-261485  11/2009
(Continued)

OTHER PUBLICATIONS

International Search Report issued Feb. 7, 2012 in International (PCT) Application No. PCT/JP2012/051091.
(Continued)

*Primary Examiner* — David Bates
(74) *Attorney, Agent, or Firm* — Wenderoth, Lind & Ponack, L.L.P.

(57) ABSTRACT

A puncture instrument has a simple configuration and can accurately control the insertion position and direction of the puncture instrument when in use to form a pilot hole in the vertebral pedicle. The puncture instrument is configured by including a puncture needle 2 for forming the pilot hole, and a reference bar 3 that is provided at the puncture needle to have a predetermined angle with respect to the puncture needle 2 and serves as a reference for guiding the puncture needle 2 to a desired position at a desired angle. With the present invention, the puncture needle 2 is guided by the reference bar 3 to a desired position at a desired angle, and hence the puncture needle can be controlled by a simple configuration as compared with the case where a guiding device is separately provided.

4 Claims, 5 Drawing Sheets

(56) References Cited

U.S. PATENT DOCUMENTS

| | | | |
|---|---|---|---|
| 4,627,425 A | 12/1986 | Reese | |
| 4,686,978 A * | 8/1987 | Wadsworth | 606/84 |
| 5,730,754 A | 3/1998 | Obenchain | |
| 6,126,664 A * | 10/2000 | Troxell et al. | 606/84 |
| 6,143,012 A * | 11/2000 | Gausepohl | 606/185 |
| 6,187,011 B1 * | 2/2001 | Torrie | 606/96 |
| 6,309,396 B1 * | 10/2001 | Ritland | 606/96 |
| 6,447,528 B2 * | 9/2002 | Paraschac | 606/190 |
| 2005/0090829 A1 | 4/2005 | Martz et al. | |
| 2005/0149091 A1 * | 7/2005 | Tanamal et al. | 606/184 |
| 2005/0177172 A1 * | 8/2005 | Acker et al. | 606/99 |
| 2008/0269756 A1 | 10/2008 | Tomko et al. | |
| 2012/0277801 A1 * | 11/2012 | Marik et al. | 606/279 |

FOREIGN PATENT DOCUMENTS

| | | |
|---|---|---|
| JP | 3165179 | 1/2011 |
| WO | WO03/057087 A2 * | 7/2003 |

OTHER PUBLICATIONS

Extended European Search Report issued Mar. 4, 2015 in corresponding European Patent Application No. 12822074.6.

* cited by examiner

PUNCTURE INSTRUMENT

TECHNICAL FIELD

The present invention relates to a puncture instrument which is used to form, in a vertebral bone, a pilot hole for embedding a pedicle screw used for spinal fusion surgery in a surgical operation of spine such as a cervical vertebra.

BACKGROUND ART

In spinal fusion surgery such as cervical vertebra fusion surgery, a method for embedding a pedicle screw in the spine is often used. The pedicle screw is embedded in such a manner that a pilot hole is formed beforehand by inserting a puncture instrument, such as a probe, and then the pedicle screw is screwed into the pilot hole.

However, in the vicinity of the spine, important organs, such as a spinal cord, a nerve root, blood vessels, and an internal organ, are located close to each other. Thus, when the position, at which the puncture instrument, such as the probe, is inserted to form a pilot hole in the cervical vertebra, is incorrect, serious damage may occur in the organs. Therefore, it is necessary to accurately determine the insertion position and direction of the puncture instrument.

Conventionally, the position of the vertebral pedicle, at which the probe is to be inserted, is checked from the front and side images of the spine captured by an X-ray apparatus, and then the probe is inserted without a guide. However, there is a problem that a variation occurs in the insertion accuracy according to the operator's experience and skills.

No technique for directly and accurately controlling the insertion position and direction of the probe has been disclosed. However, in relation to the technique, the present applicants have proposed a boring instrument guiding device which is used to form a pilot hole in a vertebral pedicle. The boring instrument guiding device is configured by including a reference pin that is used as a reference by being inserted into the vertebral arch from the posterior side to the anterior side of the spine, and an arm extending sideward from the proximal end side of the reference pin, and is configured such that a plurality of guide holes respectively opened toward the tip position of the reference pin to guide a boring instrument, such as an awl and a tap, are formed in the arm in a radial pattern (see Japanese Patent Laid-Open No. 2009-261485).

Further, in Japanese Utility Model Publication No. 3165179 different from Japanese Patent Laid-Open No. 2009-261485, there is proposed an insertion instrument guiding device for vertebral pedicle applications, which is used to more accurately guide the insertion position and angle of a pedicle screw when the pedicle screw is inserted into the vertebral pedicle. The insertion instrument guiding device is configured by including a fixed indication needle, a movable indication needle that is capable of adjusting the separation distance from the fixed indication needle, a reference line-positioning pin that is incorporated in a link mechanism so as to be positioned just at the midpoint of the separation distance between the needles, and an insertion guide section that sets and adjusts the insertion angle of the insertion instrument into the vertebral pedicle by being slid while maintaining a circular state with respect to the insertion position of the vertebral pedicle, the position being indicated by the fixed indication needle, and is configured such that, when the reference line-positioning pin is adjusted to the position of the spinous process, the insertion position and the insertion angle of the insertion instrument into the vertebral pedicle are guided with reference to the spinous process.

However, Japanese Patent Laid-Open No. 2009-261485 proposes the guiding device used in the case where an awl or a tap is used as a puncture instrument, and Japanese Utility Model Publication No. 3165179 proposes a guiding device which guides the insertion of a pedicle screw. Japanese Patent Laid-Open No. 2009-261485 and Japanese Utility Model Publication No. 3165179 both relate to important guiding devices for accurately guiding the insertion position and direction of a puncture instrument. However, there has been a request for a puncture instrument, such as a probe, which has a simple configuration formed by a metallic needle like an ice pick having a pointed tip, and which can accurately guide the insertion position and direction of the puncture instrument even when, without the use of the guiding device, a pilot hole is formed in a vertebral pedicle by using the puncture instrument.

SUMMARY OF THE INVENTION

In view of the above, an object of the present invention is to provide a puncture instrument which has a simple configuration and which, when a pilot hole is formed in a vertebral pedicle, can accurately control the insertion position and direction of the puncture instrument into the vertebral pedicle.

In order to achieve the above described object, the present invention is to provide a puncture instrument for forming, in a vertebral pedicle, a pilot hole for embedding a pedicle screw, the puncture instrument including a puncture needle for forming the pilot hole, and a reference bar that is provided at the puncture needle to have a predetermined angle with respect to the puncture needle and serves as a reference for guiding the puncture needle to a desired position at a desired angle.

With the above-described configuration, in addition to the puncture needle, the reference bar, having a predetermined angle with respect to the puncture needle, is provided at the puncture instrument itself, so that the puncture needle is guided by the reference bar to a desired position at a desired angle. Thereby, the puncture needle can be guided to a desired position by a simple configuration as compared with the conventional case where a guiding device is provided separately from a puncture instrument.

In this case, the length from the proximal end to the distal end of the reference bar can be set so that the tip of the puncture needle is located on a straight line which intersects perpendicularly with the longitudinal axis of the reference bar at the distal end of the reference bar.

Thereby, the tip of the puncture needle is formed to be located on the perpendicular of the reference bar, and hence it is found that, even when the tip of the puncture needle is in the inside of a vertebral bone during the operation for forming a pilot hole in the vertebral bone, the distal end position of the reference bar corresponds to the tip position of the puncture needle.

The reference bar can also be fixed to the puncture needle in a swingable manner at a desirable angle. However, among the vertebral bones, the cervical vertebrae are small as compared with the thoracic vertebra and the lumbar vertebrae, and hence a puncture needle for forming a pilot hole in the cervical vertebrae from a third cervical vertebra to a seventh cervical vertebra has a small diameter. Therefore, the puncture instrument can be more easily manufactured when the reference bar is provided at the puncture needle at a fixed angle, rather than when the reference bar is provided at the puncture needle at an adjustable angle. That is, a structure in which the proximal end section of the reference bar is fixed to the side surface of the puncture needle at a predetermined angle is advantageous in terms of manufacture.

As to an optimum insertion position of the puncture needle, the present inventor considers that, in a vertebral bone including an anterior vertebral body and a posterior vertebral arch, the intersection of the tangent of the posterior surface of the vertebral body and the perpendicular at the outer edge of the vertebral foramen (vertebral canal) is a puncture needle-passing point of high safety (hereinafter, may be referred to as point S). The insertion angle may be set so that the puncture needle passes through the passing point S. As to the predetermined angles, puncture instruments having an arbitrary angle in the range of 30 degrees to 60 degrees may be prepared so that an optimal puncture instrument is used according to the shape of a vertebral bone.

The reference of the reference bar is set to, for example, a line in parallel with the tangent of the posterior surface of the vertebral body. The tangent of the posterior surface of the vertebral body can be found out by the measurement based on a CT (Computed Tomography) image obtained during the operation. On the basis of the measurement, a puncture instrument is selected which has a reference bar and a puncture needle both forming a predetermined angle that allows the puncture needle to pass through the above-described point S when the reference bar of the puncture instrument is set in parallel with the tangent of the posterior surface of the vertebral body. Then, a pilot hole is formed in the vertebral pedicle by using the selected puncture instrument in such a manner that the puncture needle is inserted into the vertebral pedicle while the reference bar is located in parallel with the tangent of the posterior surface of the vertebral body.

At this time, it is preferred to provide auxiliary means for making the reference bar coincide with a predetermined reference. When the auxiliary means is adopted, the reference bar can be easily made to coincide with the predetermined reference.

As the auxiliary means, a configuration can be exemplified, which includes, at the distal end section and the proximal end section of the reference bar, a first auxiliary bar and a second auxiliary bar that are respectively projected in the directions perpendicular to the reference bar and opposite to each other.

In this configuration, for example, when the reference bar is held horizontally with respect to the posterior surface of the vertebral body, the first auxiliary bar and the second auxiliary bar, which are respectively provided at the distal end section and the proximal end section of the reference bar, project in the left and right directions, respectively. Therefore, in an X-ray radioscopic image taken from the side of the cervical vertebra, the first auxiliary bar and the second auxiliary bar are arranged side by side on a straight line as long as the reference bar is held in the horizontal state. When the reference bar is inclined from the horizontal state, both the auxiliary bars are not located side by side on the straight line and are shifted from each other in the vertical direction in the X-ray radioscopic image. Therefore, the horizontal state of the reference bar can be confirmed by the two auxiliary bars.

Further, the first auxiliary bar and the second auxiliary bar can be formed so as to respectively project from the reference bar in the directions opposite to each other. Thereby, both the auxiliary bars respectively project from both sides of the reference bar, and hence it is possible to easily discriminate the inclination of the reference bar.

It is preferred that the puncture instrument described above is used to form a pilot hole in a vertebral bone of one of a third cervical vertebra to a seventh cervical vertebra. Although these vertebral bones are smaller than the other vertebral bones, a pilot hole can be accurately formed at a predetermined position at a predetermined angle by the use of the puncture instrument having the simple configuration.

Note that the puncture instrument of the present invention can be used not only to form a pilot hole in a cervical vertebra but also to form a pilot hole in a vertebral pedicle of another vertebral bone, such as a lumbar vertebra and a thoracic vertebra.

As described above, according to the present invention, the reference bar is provided at the puncture needle at a predetermined angle so that the puncture needle is guided by the reference bar to a desired position at a desired angle, and hence it is not necessary that a guiding device is separately provided as in the conventional case. Also, the insertion position and direction into a vertebral pedicle can be accurately controlled by a simple configuration.

DESCRIPTION OF EMBODIMENTS

In the following, embodiments according to the present invention will be described with reference to the accompanying drawings.

First Embodiment

Figure 1:
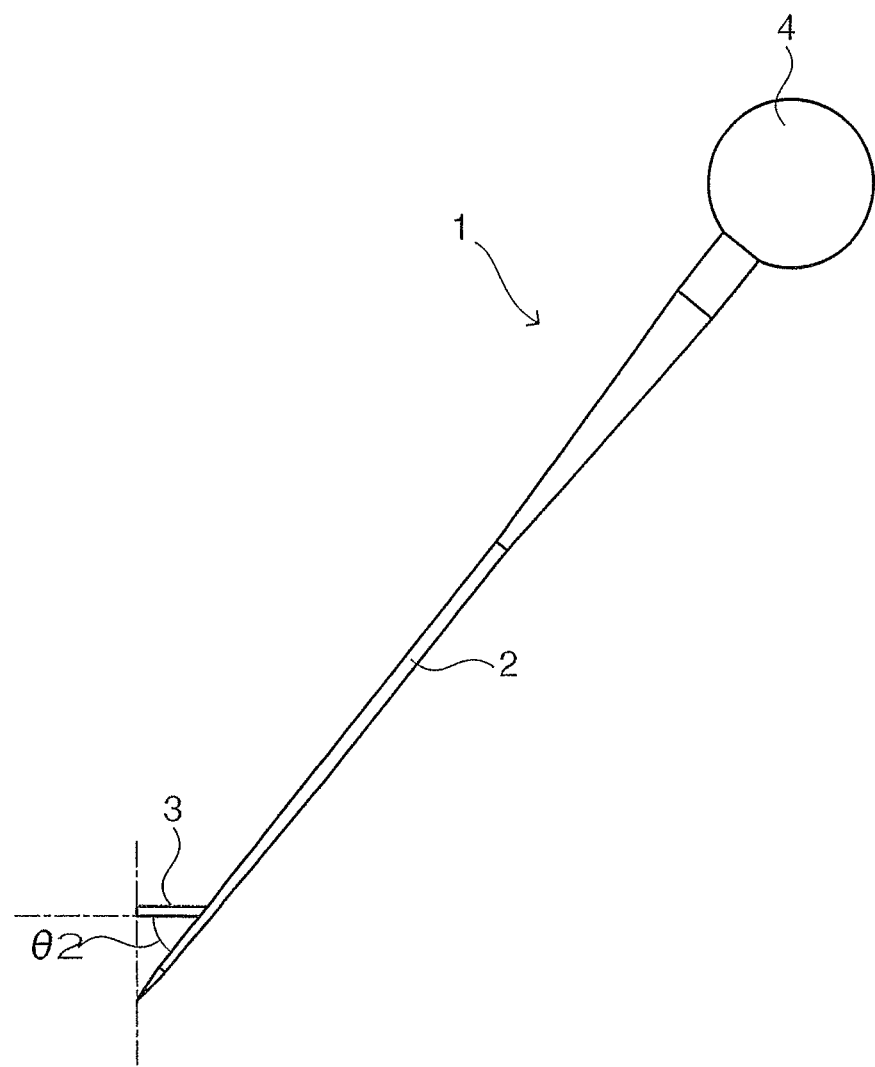
FIG. 1 is a schematic view showing a puncture instrument of a first embodiment.
Figure 2:
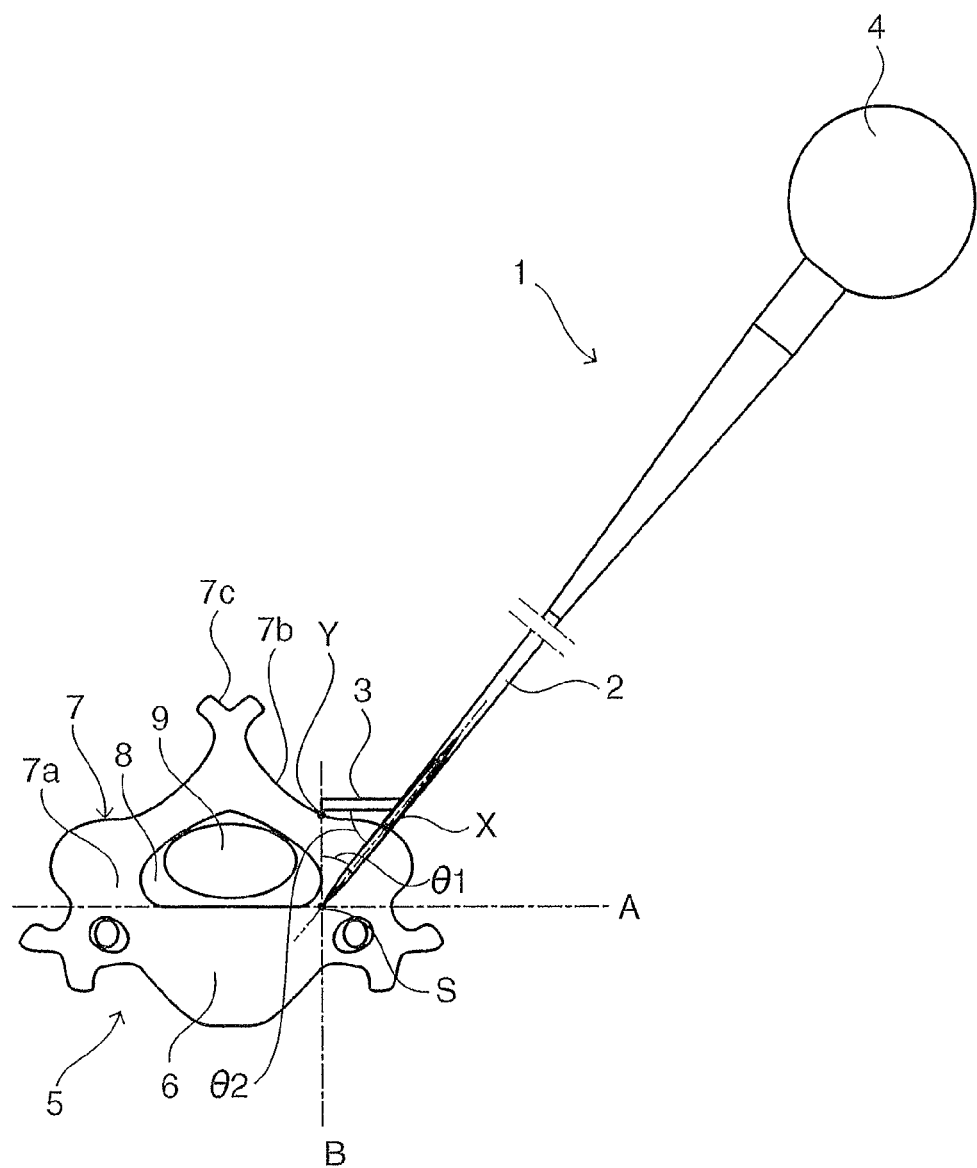
FIG. 2 is a view showing a use state of the puncture instrument of the first embodiment.
Figure 3:
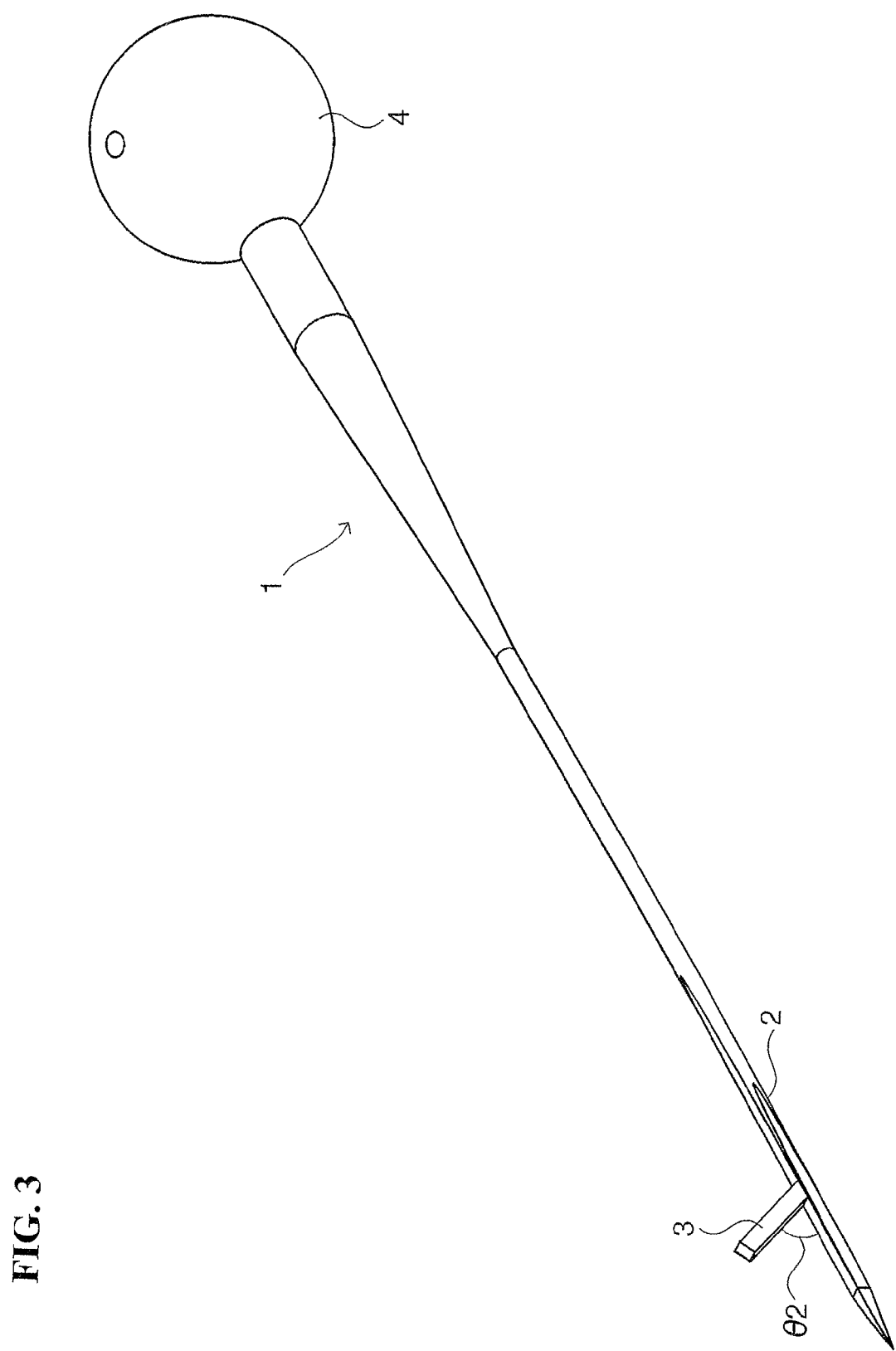
FIG. 3 is a perspective view showing the puncture instrument of the first embodiment.
Figure 4:
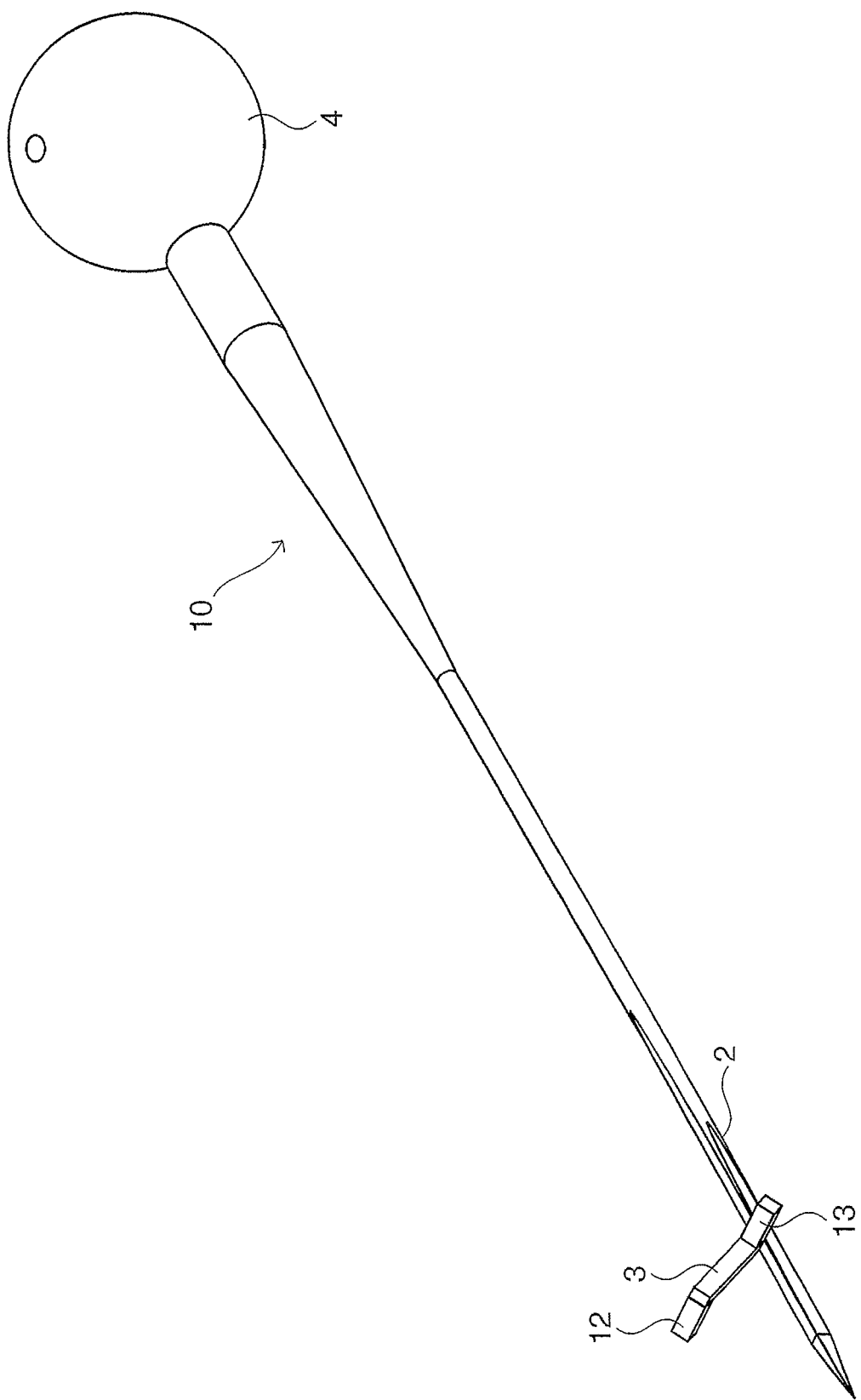
FIG. 4 is a perspective view showing a puncture instrument of a second embodiment.
Figure 5A:
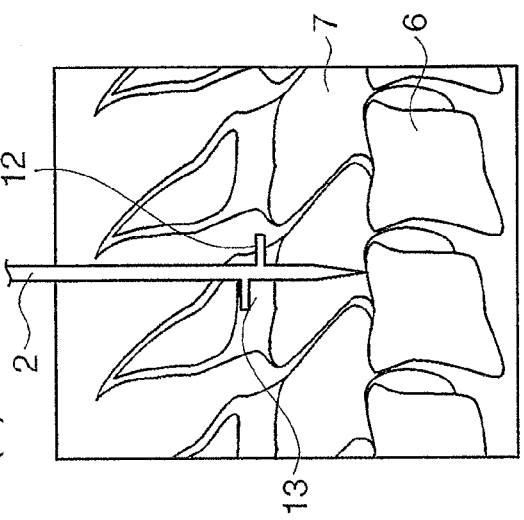
FIGS. 5(a)-5(f) are views showing a use state of the second embodiment, with FIG. 5(a) showing an X-ray image photographed from the side and showing a state where the insertion angle of a puncture needle into a vertebral pedicle is too large, FIG. 5(b) showing a CT sectional view of a vertebral bone in the state of FIG. 5(a), FIG. 5(c) showing an X-ray image photographed from the side and showing a state where the insertion angle of the puncture needle into the vertebral pedicle is appropriate, FIG. 5(d) showing a CT sectional view of the vertebral bone in the state of FIG. 5(c), FIG. 5(e) showing an X-ray image photographed from the side and showing a state where the insertion angle of the puncture needle into the vertebral pedicle is too small, and FIG. 5(f) showing a CT sectional view of the vertebral bone in the state of FIG. 5(e).
Figure 5C:
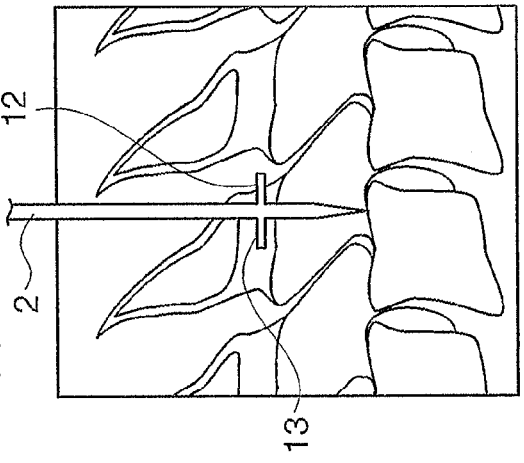
Figure 5E:
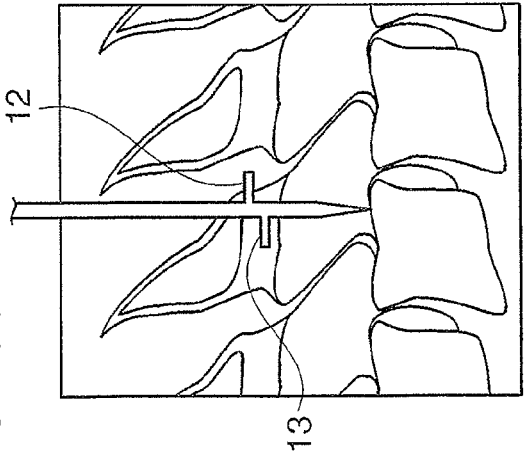
Figure 5B:
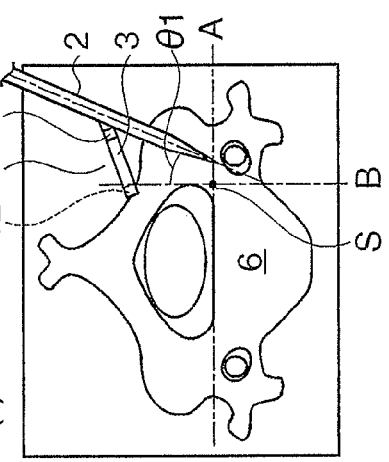
Figure 5D:
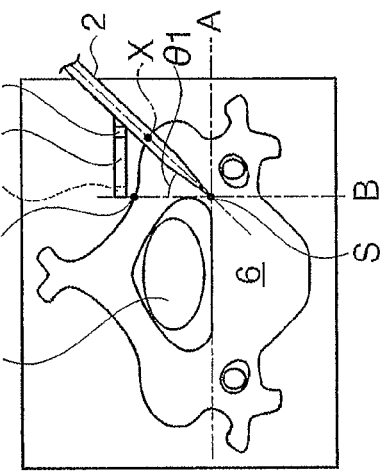
Figure 5F:
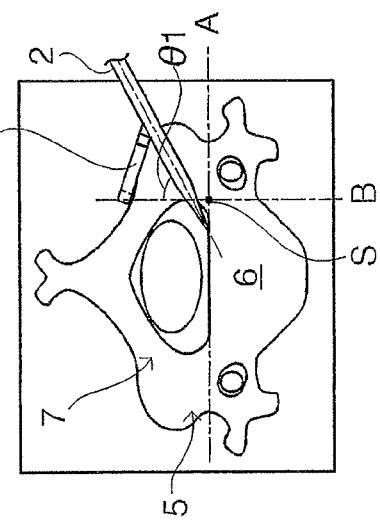

As shown in FIG. 1 to FIG. 3, a puncture instrument 1 according to a first embodiment is used to form a pilot hole for embedding a pedicle screw, in a vertebral pedicle of one of third to seventh cervical vertebrae of a spine. The puncture instrument 1 includes a puncture needle 2 which is used to form a pilot hole in a vertebral pedicle, and a reference bar 3 which is provided at the puncture needle 2 to have a predetermined angle θ2 with respect to the puncture needle 2 and which serves as a reference to guide the puncture needle 2 to a desired position at a desired angle.

The puncture needle 2, which is referred to as a so-called probe, includes a metallic needle having a pointed tip and is used to form a small pilot hole before the formation of a tap for embedding a pedicle screw in the vertebral pedicle. The puncture needle 2 is made of, for example, stainless steel, and includes a spherical operation handle section 4 at the proximal end section thereof. The insertion position and the insertion direction of the tap are controlled by the pilot hole formed in the vertebral pedicle, so that the embedding position of the pedicle screw is determined.

The proximal end section of the puncture needle 2 in this example is formed to have a circular cross section, and the portion from the middle section to the distal end section of the puncture needle 2 is formed in a shape having a quadrangular cross section and pointed toward the distal end of the puncture needle 2. The quadrangular shape of the cross section is a square shape or a rectangular shape. The puncture needle 2 is formed to have a diameter of 3 mm to 5 mm at the proximal end section thereof, and is formed to have a quadrangular cross section at the distal end section thereof so as to be tapered toward the distal end thereof. The cross sectional shape of the puncture needle 2 is not limited to that of the present example generally as long as the puncture needle 2 is a puncture needle having a pointed tip.

The reference bar 3 fixed to the puncture needle 2 is formed in a straight shape, and is welded to the distal end section of the puncture needle 2 at a predetermined angle θ2 with respect to the puncture needle 2.

The fixing position of the reference bar 3 is set such that, when the tip of the puncture needle 2 reaches a desired insertion position, for example, when the tip of the puncture needle 2 is inserted in the vertebral arch to reach the vertebral body, the reference bar 3 is brought into a fixed position in contact with the vertebral arch so as not to hinder the insertion of the puncture needle 2. The target arrival position of the puncture needle 2 is not limited to the position at which the tip of the puncture needle 2 reaches the vertebral body, and can also be set at the base of the vertebral pedicle when the puncture instrument is used to form a pilot hole for a screw. In the present example, the fixing position of the reference bar 3 is set to a position of 15 mm to 35 mm from the tip of the puncture needle 2. However, the fixing position of the reference bar 3 is not limited to this position.

The reference bar 3 is made of stainless steel similarly to the puncture needle 2, and is formed to have a cross section of, for example, a quadrangular shape so that the inclination of the puncture needle 2 in the direction of the vertebral canal can also be easily visualized in X-ray radioscopic imaging. However, examples of the cross sectional shape of the reference bar 3 may include, but are not particularly limited to, a circular shape, an elliptical shape, a square shape, and the like.

The length from the proximal end to the distal end of the reference bar 3 is set so that the tip of the puncture needle 2 is positioned on an extension of a line perpendicularly intersecting with the reference bar 3 at the distal end of the reference bar 3. This is because, with the configuration in which the tip of the puncture needle 2 is located on the vertical line of the reference bar 3, the tip position of the puncture needle 2 can be known even when the tip of the puncture needle 2 is inside the vertebral bone during the operation to form a pilot hole in the vertebral bone. The reference bar 3 of the present example is set at a position of 15 mm to 35 mm from the tip of the puncture needle 2, and hence the length of the reference bar 3 is set to about 10 mm to about 20 mm. However, the length of the reference bar is changed according to the length from the tip of the puncture needle to the position at which the reference bar is fixed to the puncture needle, and hence the length of the reference bar is not limited to the length of the present example.

The proximal end section of the reference bar 3 is welded and fixed on the side surface of the puncture needle 2 at a predetermined angle with respect to the puncture needle 2. When some seven kinds of the puncture instruments 1 having predetermined angles θ2 which are five degrees apart from each other, like 30 degrees, 35 degrees, 40 degrees, 45 degrees, 50 degrees, 55 degrees, and 60 degrees, are prepared, an optimum insertion angle can be selected according to the shape of vertebral bone. Of course, a puncture instrument having a predetermined angle other than the above-described angles may also be prepared.

A method for forming a pilot hole by using the puncture instrument 1 having the above-described configuration in a spinal fusion surgery performed through the posterior surgical exposure will be specifically described. First, a cross-sectional structure of a vertebral bone 5 is described with reference to FIG. 2. As shown in FIG. 2, the vertebral bone 5 includes a vertebral body 6 located on the anterior side, and a vertebral arch 7 located on the posterior side. The vertebral arch 7 is a scale-like section extending toward the posterior side from the vertebral body 6, and includes a vertebral pedicle 7a connected to the vertebral body 6, and a lamina of vertebral arch 7b having a shape such as a shape formed by bending the lamina on the posterior side of the vertebral pedicle 7a. The laminas of vertebral arch 7b are combined together in the midline to form a spinous process 7c extending toward the posterior side. A large hole surrounded by the vertebral body 6 and the vertebral arch 7 is a vertebral foramen 8, through which the spinal cord 9 passes, and the vertical sequence of the vertebral foramens 8 is referred to as the vertebral canal.

As shown in FIG. 2, an intersection S between the tangent A of the posterior surface of the vertebral body 6 and the perpendicular B of the outer edge of the vertebral foramen 8 (vertebral canal) is obtained from a CT (Computed Tomography) image. Since this intersection S is the target point S, a straight line is drawn in parallel with the inclination of the vertebral pedicle 7a from the target point S, and the insertion angle θ1 of the puncture needle 2 is obtained from the straight line. Then, a puncture instrument 1 is selected that has an inclination angle θ2 between the reference bar 3 and the puncture needle 2, which angle corresponds to the insertion angle. The insertion angle θ1 is an angle formed between the central axis of the puncture needle 2 and the perpendicular B, and is the complementary angle of the inclination angle θ2.

Next, a mark is formed at the intersection X of an extension of the straight line passing through the point S in parallel with the inclination of the vertebral pedicle 7a, and the surface of the lamina of vertebral arch 7b, or the like, and the intersection X is set as the insertion position (point). Further, a mark is formed at the intersection Y of a perpendicular B drawn from the target point S and the surface of the lamina of vertebral arch 7b, or the like.

Then, the puncture needle 2 of the puncture instrument 1 having a suitable inclination is set at the insertion point X, and is inserted into the vertebral pedicle while the reference bar 3 is adjusted visually (or on the basis of an X-ray radioscopic image taken from the side of the vertebral pedicle) so as to be set in the horizontal direction in parallel with the tangent of the posterior surface of the vertebral body.

Thereby, as long as the reference bar 3 is horizontally held, the insertion angle θ1 of the puncture needle 2 is not changed, and hence the puncture needle 2 reaches the point S of high safety.

At this time, the tip of the puncture needle 2 is inside the vertebral bone 5 (vertebral pedicle 7a), and hence the reaching of the tip of the puncture needle 2 to the target point S is determined on the basis of the position of the distal end of the reference bar 3. That is, the tip of the puncture needle 2 is located on the vertical line drawn at the distal end position of the reference bar 3. Therefore, as long as the reference bar 3 is horizontally held, the tip of puncture needle 2 is located on the line which is perpendicular to the reference bar 3 and which is drawn from the distal end of the reference bar 3. From the X-ray radioscopic image (see, for example, FIGS. 5(*a*), (*c*) and (*e*)) taken from the side of the vertebral bone 5, it can be seen that the tip position of the puncture needle 2 reaches the target point S when the mark Y formed on the surface of the lamina of vertebral arch 7*b* from the posterior side coincides with the distal end position of the reference bar 3 in the vertical line direction at the reaching of the tip of the puncture needle 2 to the posterior surface of the vertebral body 6.

As described above, the present embodiment is configured such that the reference bar 3 is provided at the puncture needle 2 to have a predetermined angle with respect to the puncture needle 2, and such that the puncture needle 2 is guided by the reference bar 3 to a desired insertion position at a desired angle. Therefore, a special guiding device for guiding the puncture needle 2 to the target position need not be separately provided, and the insertion position and direction of the puncture needle 2 into the vertebral pedicle 7*a* can be accurately controlled with a simple configuration.

Second Embodiment

In a puncture instrument 10 of a present embodiment, the following configuration is added to the puncture instrument 1 of the first embodiment. That is, the puncture instrument 10 of the present embodiment is provided with auxiliary means 11 for making the reference bar 3 coincide with a predetermined reference.

Here, the predetermined reference is, similarly to the first embodiment, a line in parallel with the tangent of the posterior surface of the vertebral body. The auxiliary means 11 includes, at the distal end section and the proximal end section of the reference bar 3, a first auxiliary bar 12 and a second auxiliary bar 13 respectively that are respectively projected in the directions perpendicular to the reference bar 3 and opposite to each other.

The length of each of the auxiliary bars 12 and 13 is set to 5 mm to 10 mm, and is set to such a length that the auxiliary bars 12 and 13 are not brought into contact with the adjacent vertebral bone 5 even when being projected in the direction of the vertebral canal. Each of the auxiliary bars 12 and 13 is formed to have a cross section of a quadrangular shape, and is set to have a width of about 1 mm to about 5 mm. Note that the cross sectional shape of the auxiliary bars 12 and 13 is not limited to the quadrangular shape, and may be a circular shape, an elliptical shape, and other polygonal shapes.

Here, the first auxiliary bar 12 and the second auxiliary bar 13 are respectively projected from the reference bar in the directions opposite to each other, but may also be configured so as to project in the same direction.

With the configuration provided with the auxiliary means 11 described above, operation effects as shown in FIG. 5 can be expected. That is, the preparation step for inserting the puncture instrument 10 into the vertebral bone is the same as the preparation step of the first embodiment, but it can be easily confirmed whether or not the reference bar 3 is held in the horizontal state after the puncture instrument 10 is inserted.

FIG. 5(*a*) is an X-ray image photographed from the side and showing a state where the insertion angle $\theta 1$ of the puncture needle into the vertebral pedicle is too large, and FIG. 5(*b*) is a CT sectional view of the vertebral bone in the state of FIG. 5(*a*). As shown in FIG. 5(*b*), even in the case where the insertion position of puncture needle 2 is the same, when the insertion angle $\theta 1$ of the puncture needle 2 with respect to the vertical line B is large, the first auxiliary bar 12 and the second auxiliary bar 13, which are respectively arranged at the distal end section and the proximal end section of the reference bar 3, are shown to be shifted from each other in the vertical direction in the X-ray photograph image. Thereby, it is found that the reference bar 3 is not in the horizontal state.

FIG. 5(*e*) is an X-ray image photographed from the side and showing a state where the insertion angle $\theta 1$ of the puncture needle into a vertebral pedicle is too small, and FIG. 5(*f*) is a CT sectional view of the vertebral bone in the state of FIG. 5(*e*). As shown in FIG. 5(*f*), even in the case where the insertion position of puncture needle 2 is the same, when the insertion angle of the puncture needle 2 with respect to the vertical line B is relatively small, the first auxiliary bar 12 and the second auxiliary bar 13, which are fixed to the reference bar 3, are shown to be shifted from each other in the vertical direction in the X-ray photograph image. Thereby, it is found that the reference bar 3 is not in the horizontal state.

FIG. 5(*c*) is an X-ray image photographed from the side and showing a state where the insertion angle $\theta 1$ of the puncture needle into the vertebral pedicle is appropriate, and FIG. 5(*d*) is a CT sectional view of the vertebral bone in the state of FIG. 5(*c*). When the insertion position of the puncture needle 2 is the same, and when the insertion angle $\theta 1$ of the puncture needle 2 with respect to the vertical line is suitable, the first auxiliary bar 12 and the second auxiliary bar 13, which are fixed to the reference bar 3, are shown on a straight line in the X-ray photograph image. Thereby, it is found that the reference bar 3 is in the horizontal state.

In this way, the first auxiliary bar 12 and the second auxiliary bar 13 are respectively arranged at the distal end section and the proximal end section of the reference bar 3. Therefore, in the X-ray radioscopic image taken from the side of the cervical vertebra, the first auxiliary bar 12 and the second auxiliary bar 13 are arranged side by side on a straight line as long as the reference bar 3 is held in the horizontal state, and hence the horizontal state of the reference bar 3 can be easily confirmed by the two auxiliary bars 12 and 13.

Not that the present invention is not limited to the above described embodiments, and numerous modifications and changes can be obviously made therein without departing from the spirit and scope of the present invention. For example, in the above-described embodiments, a case where a probe is used as the puncture needle is exemplified, but the present invention is not limited to this. When the present invention is also applied to other puncture needles, such as an awl and a screw tap, each of the puncture needles can be accurately guided to a target position without a guiding device being separately provided.

The invention claimed is:

1. A puncture instrument for forming, in a vertebral pedicle, a pilot hole for embedding a pedicle screw the puncture instrument comprising:
    a puncture needle for forming the pilot hole;
    a reference bar attached to the puncture needle for guiding the puncture needle to a desired position at a desired angle with respect to the vertebral pedicle; and
    auxiliary parts for use in making the reference bar coincide with a predetermined reference location of the vertebral pedicle;
    wherein the puncture needle is longitudinally elongated so as to have a longitudinal axis;
    wherein the puncture needle has a puncture needle proximal end, and a puncture needle distal end remote from the puncture needle proximal end;

wherein the puncture needle has an operation section at the puncture needle proximal end;

wherein the puncture needle has a needle point at the puncture needle distal end;

wherein the reference bar has first and second opposite extreme ends and is a straight bar from said first extreme end to said second extreme end;

wherein one of the first and second extreme ends of the reference bar constitutes a reference bar proximal end, and the other of the first and second extreme ends constitutes a reference bar distal end remote from the reference bar proximal end;

wherein the reference bar proximal end is fixed to the puncture needle at a location of the puncture needle intermediate the puncture needle proximal end and the puncture needle distal end;

wherein the reference bar is fixed to the puncture needle so as to form a predetermined fixed angle between the longitudinal axis of the puncture needle and a longitudinal axis of the straight bar constituting the reference bar;

wherein the predetermined fixed angle is in a range of 30 degrees to 60 degrees; and wherein the reference bar has a length such that the reference bar is disposed perpendicular to a line intersecting both the needle point of the puncture needle and said one of the first and second extreme ends of the reference bar that constitutes the reference bar distal end;

wherein the auxiliary parts comprise a first auxiliary bar and a second auxiliary bar, respectively;

wherein the first auxiliary bar is fixed to and projects away from the reference bar distal end, and the second auxiliary bar is fixed to and projects away from the reference bar proximal end; and wherein the first and second auxiliary bars are both perpendicular to the straight bar constituting the reference bar.

2. The puncture instrument according to claim 1, wherein the first and second auxiliary bars project in mutually opposite directions perpendicularly away from the straight bar constituting the reference bar.

3. The puncture instrument according to claim 2, wherein the operation section of the puncture needle has a spherical operation handle thereon.

4. The puncture instrument according to claim 1, wherein the operation section of the puncture needle has a spherical operation handle thereon.

* * * * *